US012778458B2

(12) United States Patent
Cho et al.

(10) Patent No.: US 12,778,458 B2
(45) Date of Patent: Nov. 3, 2026

(54) RESPIRATORY SENSING DEVICE AND METHOD OF USING THE RESPIRATORY SENSING DEVICE

(71) Applicant: ATSENS CO., LTD., Gyeonggi-do (KR)

(72) Inventors: Seung Bum Cho, Gyeonggi-do (KR); Kyu Jin Lee, Gyeonggi-do (KR); Ho Il Lee, Gyeonggi-do (KR); Ji Min Cho, Gyeonggi-do (KR); Sang Hyun Kim, Gyeonggi-do (KR); Jong Ook Jeong, Gyeonggi-do (KR)

(73) Assignee: ATSENS CO., LTD., Gyeonggi-Do (KR)

( * ) Notice: Subject to any disclaimer, the term of this patent is extended or adjusted under 35 U.S.C. 154(b) by 170 days.

(21) Appl. No.: 18/790,779

(22) Filed: Jul. 31, 2024

(65) Prior Publication Data

US 2025/0160689 A1 May 22, 2025

(30) Foreign Application Priority Data

Nov. 16, 2023 (KR) ........................ 10-2023-0159477

(51) Int. Cl.
*A61B 5/113* (2006.01)
*A61B 5/00* (2006.01)
(Continued)

(52) U.S. Cl.
CPC ............ *A61B 5/1135* (2013.01); *A61B 5/259* (2021.01); *A61B 5/6823* (2013.01);
(Continued)

(58) Field of Classification Search
CPC ....... A61B 5/28; A61B 5/6823; A61B 5/6832; A61B 5/6833; A61B 5/1135
See application file for complete search history.

(56) References Cited

U.S. PATENT DOCUMENTS

2003/0045806 A1 3/2003 Brydon
2008/0319277 A1* 12/2008 Bradley ................ A61B 7/003 600/301
(Continued)

FOREIGN PATENT DOCUMENTS

JP 2001525706 A 12/2001
JP 2003275185 A 9/2003
(Continued)

OTHER PUBLICATIONS

Japanese Office Action for Corresponding JP Application No. 2024-175087 mailed May 16, 2025, 5 pages.
(Continued)

*Primary Examiner* — Eun Hwa Kim
(74) *Attorney, Agent, or Firm* — Bridgeway IP Law Group, PLLC; Sang Ho Lee; Hyun Woo Shin

(57) ABSTRACT

A respiratory sensing device includes a housing including a structure in an inner space thereof, wherein a battery is provided in the structure, a flexible substrate, wherein the housing is disposed on and connected to one surface of the flexible substrate and a plurality of respiration sensor electrodes are disposed on the flexible substrate, and an adhesive member having a predetermined thickness, including an opening portion through which the plurality of respiration sensor electrodes are exposed, disposed on another surface of the flexible substrate, and configured to attach the flexible substrate to skin.

18 Claims, 21 Drawing Sheets

(51) Int. Cl.
*A61B 5/259* (2021.01)
*A61M 16/00* (2006.01)

(52) U.S. Cl.
CPC ....... *A61B 5/6833* (2013.01); *A61M 16/0003* (2014.02); *A61B 2562/043* (2013.01); *A61B 2562/164* (2013.01); *A61M 2016/0018* (2013.01)

(56) References Cited

U.S. PATENT DOCUMENTS

| | | | | |
|---|---|---|---|---|
| 2009/0281394 | A1* | 11/2009 | Russell | A61B 5/0002 600/301 |
| 2010/0063365 | A1 | 3/2010 | Pisani et al. | |
| 2011/0066062 | A1* | 3/2011 | Banet | A61B 5/113 600/534 |
| 2013/0066168 | A1 | 3/2013 | Yang et al. | |
| 2014/0228657 | A1* | 8/2014 | Palley | A61B 5/0816 600/533 |
| 2018/0220962 | A1* | 8/2018 | Palley | A61B 5/0004 |
| 2019/0022400 | A1 | 1/2019 | Kumar et al. | |
| 2020/0229706 | A1* | 7/2020 | Nishimura | A61B 5/6832 |
| 2020/0352510 | A1 | 11/2020 | Dhillon et al. | |
| 2021/0000383 | A1 | 1/2021 | Hussain et al. | |
| 2022/0007965 | A1 | 1/2022 | Tiron et al. | |
| 2024/0041411 | A1 | 2/2024 | Cho et al. | |
| 2024/0091545 | A1 | 3/2024 | Kumar et al. | |
| 2024/0277280 | A1* | 8/2024 | Al-Ali | A61B 5/0006 |

FOREIGN PATENT DOCUMENTS

| | | | |
|---|---|---|---|
| JP | 2005074012 | A | 3/2005 |
| JP | 2009500047 | A | 1/2009 |
| JP | 2013534833 | A | 9/2013 |
| JP | 2022507834 | A | 1/2022 |
| JP | 2022024101 | A | 2/2022 |
| KR | 102188134 | B1 | 12/2020 |
| KR | 1020220007872 | | 1/2022 |
| KR | 102395864 | B1 | 5/2022 |
| KR | 102488621 | B1 | 1/2023 |
| KR | 1020230130491 | A | 9/2023 |
| WO | 1998052467 | A1 | 11/1998 |
| WO | 2006109072 | A1 | 10/2006 |

OTHER PUBLICATIONS

Notice of Non-Final Rejection for Corresponding Korean Application No. KR-10-2023-0159477, Mar. 19, 2024, 7 pgs.

* cited by examiner

RESPIRATORY SENSING DEVICE AND METHOD OF USING THE RESPIRATORY SENSING DEVICE

CROSS-REFERENCE TO RELATED APPLICATION

This application claims the benefit of Korean Patent Application No. 10-2023-0159477, filed on Nov. 16, 2023, in the Korean Intellectual Property Office, the disclosure of which is incorporated herein in its entirety by reference.

BACKGROUND

1. Field

The disclosure relates to a respiratory sensing device, and more particularly, to a respiratory sensing device having a structure that is attached to a user's skin and includes an air layer between the skin and a respiratory sensing electrode to thus detect a change in capacitance due to expansion or contraction of the abdomen, chest, or the like according to breathing.

2. Description of the Related Art

In order to diagnose sleep apnea, polysomnography (PSG), home sleep apnea test (HSAT), continuous positive airway pressure (CPAP), ApneaLnk, Actigraphy, and the like may be used.

Polysomnography diagnoses sleep apnea using sensors that monitor brain activity, eye movement, heart rate, blood oxygen levels, air flow, respiratory rate, and muscle activity. Polysomnography determines whether a patient has sleep apnea based on values measured during the patient's sleep. In polysomnography, data on the user's sleep pattern is obtained using data sensed through sensors, and sleep apnea is diagnosed based on the data on the sleep pattern. Home sleep apnea test diagnoses sleep apnea by monitoring fewer parameters than polysomnography. In home sleep apnea test, sleep apnea is diagnosed by sensing values that measure the air flow, heart rate, respiratory rate, and blood oxygen levels. Here, the respiratory rate is a basic signal to diagnose sleep apnea.

As a user has to sleep while wearing a plurality of sensors, this may cause discomfort. Sleep apnea may not be tested accurately due to the user's discomfort.

The background technology described above is technical information that the inventor possessed for the derivation of the present disclosure or acquired in the derivation process of the present disclosure, and it cannot be said that it is known technology disclosed to the general public before the filing of the present disclosure.

SUMMARY

Provided is a respiratory sensing device having a structure that is attached to a user's skin and includes an air layer between the skin and a respiratory sensing electrode to thus detect a change in capacitance due to expansion or contraction of the abdomen, chest, or the like according to breathing.

However, such an objective is just an example, and the objective to be solved by the disclosure is not limited thereto.

According to an aspect of the disclosure, a respiratory sensing device includes a housing including a structure in an inner space thereof, wherein a measuring electronics is provided in the structure, a flexible substrate, wherein the housing is disposed on and connected to one surface of the flexible substrate, and a plurality of respiration sensor electrodes are disposed on the flexible substrate, and an adhesive member having a certain thickness, including an opening portion through which the plurality of respiration sensor electrodes are exposed, disposed on another surface of the flexible substrate, and configured to attach the flexible substrate to skin. Here, a battery provide power to the measuring electronics, which may be located inside the housing for a single-use or outside housing for easy-to-replace.

The plurality of respiration sensor electrodes may be located on the flexible substrate in an area where the housing is not located.

According to embodiments, the respiratory sensing device may further include a cover member arranged to cover the opening portion and implemented with a high dielectric elastic material.

The flexible substrate may further include at least one electrocardiogram electrode at a position corresponding to the housing.

The adhesive member may further include a conductive hole area at a position corresponding to the electrocardiogram electrode to allow the electrocardiogram electrode to be electrically connected to the skin. A conductive gel, such as hydrogel, may be covered over the conductive area.

The respiration sensor electrodes may not be directly attached to the skin through the opening portion.

According to embodiments, the respiratory sensing device may further include a connection portion disposed on the flexible substrate.

According to embodiments, the respiratory sensing device may be electrically connected to at least one of an external temperature sensor, an acceleration sensor, a microphone, and an electrocardiogram sensor, through the connection portion, to receive measurement values.

According to embodiments, the respiratory sensing device may be connected to an external nasal breathing device, through the connection portion, to check air discharged from user's nose.

According to embodiments, an air layer may be formed between the plurality of respiration sensor electrodes and the skin through the opening portion, and the plurality of respiration sensor electrodes may measure a capacitance value corresponding to a change in the size of abdomen or chest according to breathing.

The plurality of respiration sensor electrodes may measure capacitance values varying according to a respiration cycle.

The plurality of respiration sensor electrodes may measure capacitance values varying according to an attachment position.

The housing may be arranged on the flexible substrate in a direction perpendicular to a direction in which the plurality of respiration sensor electrodes are arranged in a row.

The plurality of respiration sensor electrodes and the housing may be arranged in a row on the flexible substrate.

According to another aspect of the disclosure, a method of using the respiratory sensing device includes attaching, through the adhesive member, the plurality of respiration sensor electrodes of the substrate at the height of a portion around user's abdomen According to another aspect of the disclosure, a computer program may be stored in a medium to execute, by using a computer, any one of the methods according to embodiments.

In addition, other methods, other systems, and a computer-readable recording medium having recorded thereon a computer program to execute the method are further provided in order to implement the disclosure.

Other aspects, features, and advantages than those described above will become apparent from the following drawings, claims, and detailed description of the disclosure.

BRIEF DESCRIPTION OF THE DRAWINGS

These and/or other aspects will become apparent and more readily appreciated from the following description of the embodiments, taken in conjunction with the accompanying drawings in which:

FIGS. 7A, 7B, and 7C illustrate examples of an adhesive member, wherein:

FIG. 7A illustrates a first embodiment of an adhesive member;

FIG. 7B illustrates a second embodiment of an adhesive member; and

FIG. 7C illustrates a third embodiment of an adhesive member;

FIGS. 11A and 11B illustrate a change of an air layer in the respiratory sensing device according to a respiration cycle, wherein:

FIG. 11A illustrates a change of an air layer in a respiratory sensing device according to a respiration cycle at an inspiration phase of respiration;

FIG. 11B illustrates a change of an air layer in a respiratory sensing device according to a respiration cycle at an expiration phase of respiration;

DETAILED DESCRIPTION

Figure 1A:
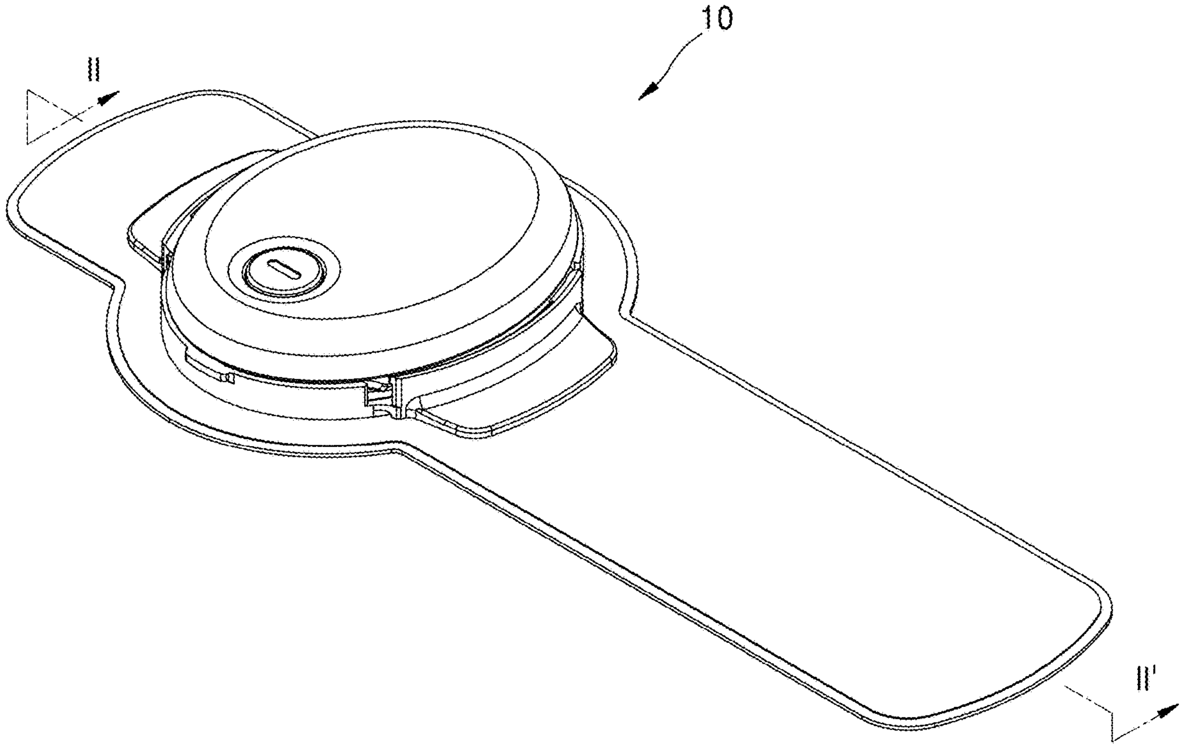
FIG. 1A illustrates a respiratory sensing device according to embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The configuration and operation of the disclosure are described below in detail with reference to embodiments illustrated in the accompanying drawings.

As the disclosure allows for various changes and numerous embodiments, embodiments will be illustrated in the drawings and described in detail in the written description. Advantages and features of the disclosure and methods of accomplishing the same may be understood more readily by reference to the following detailed description of exemplary embodiments and the accompanying drawings. However, the present embodiments may be implemented in various forms, not by being limited to the embodiments presented below.

Hereinafter, embodiments will be described in detail with reference to the accompanying drawings, and in the description with reference to the drawings, the same or corresponding constituents are indicated by the same reference numerals and redundant descriptions thereof are omitted.

In the following embodiment, when a constituent element is disposed "above" or "on" to another constituent element, the constituent element may be only directly on the other constituent element or above the other constituent elements in a non-contact manner In the following embodiment, it will be understood that although the terms first, second, etc. may be used herein to describe various elements, these elements should not be limited by these terms. These elements are only used to distinguish one element from another.

In the following embodiment, as used herein, the singular forms "a," "an," and "the" are intended to include the plural forms as well, unless the context clearly indicates otherwise.

In the following embodiment, it will be further understood that the terms "comprises" and/or "comprising" used herein specify the presence of stated features or elements, but do not preclude the presence or addition of one or more other features or components.

Sizes of elements in the drawings may be exaggerated for convenience of explanation. For example, since sizes and thicknesses of elements in the drawings are arbitrarily illustrated for convenience of explanation, the following embodiments are not limited thereto.

Figure 1B:
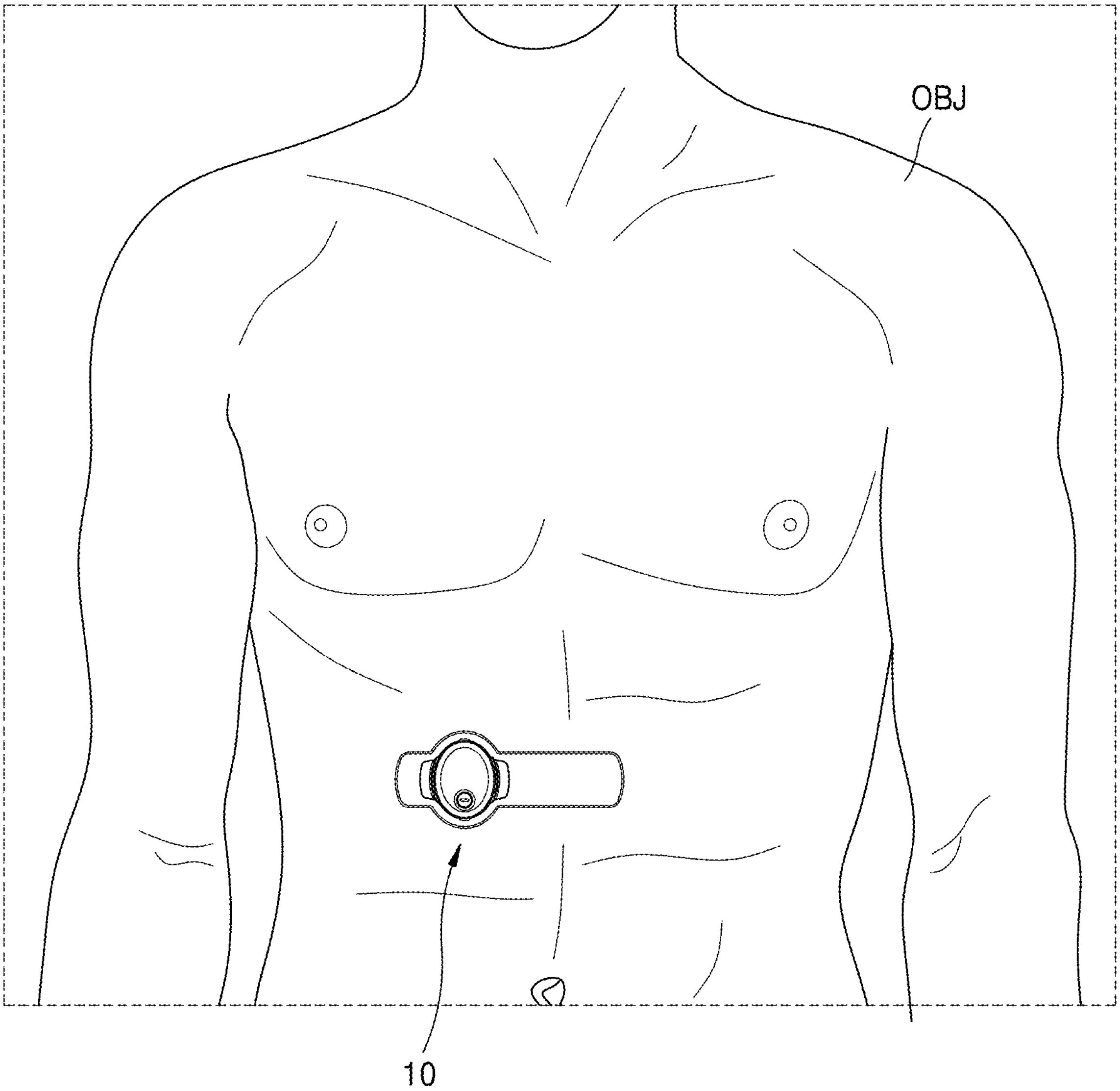
FIG. 1B illustrates the respiratory sensing device attached to a user's skin according to embodiments.

Furthermore, terms such as " . . . portion," " . . . unit," " . . . module," and " . . . block" stated in the specification may signify a unit to process at least one function or operation FIG. 1A illustrates a respiratory sensing device 10 according to embodiments, and FIG. 1B illustrates the respiratory sensing device 10 attached to a user's skin according to embodiments.

The respiratory sensing device 10 according to embodiments may be a device that is attached to a location adjacent to the user's abdomen or chest, to sense respiration information of a user. Depending on breathing of the user, the user's body organs, such as the abdomen and the chest, expand during inspiration and contract during exhalation. The respiratory sensing device 10 is attached to the user's body through an adhesive member and does not have an adhesive member at a position where a respiratory sensing electrode is exposed, allowing a certain air layer to exist between the respiratory sensing electrode and the skin. In order to have the air layer, the adhesive member may have a certain thickness. The thickness of the adhesive member may be, for example, 0.5 mm or more, in particular 0.6 mm. The disclosure is not limited thereto, and the adhesive member may be implemented in various thicknesses. When the user's body expands with respiration, the air layer between the respiratory sensing electrode and the skin decreases, and when the user's body contracts with respiration, the air layer between the respiratory sensing electrode and the skin increases. Changes in the volume of the air layer or size of the air layer adjacent to the respiratory sensing electrode may change the value of capacitance detected by the respiratory sensing electrode. The respiratory sensing device 10 may sense a change in value of capacitance detected by the respiratory sensing electrode. The respiratory sensing device 10 may obtain information about a respiration time point, a respiration cycle, and the like from the change in the capacitance value.

The respiratory sensing device 10 may be attached at a position in the user's body, where a change according to breathing is noticeable. The respiratory sensing device 10 may be attached at a certain attachment position, for example, the abdomen, the chest, and the like. The respiratory sensing device 10 may have the respiratory sensing electrode attached to the abdomen in a horizontal direction and may sense a change value of capacitance according to a change in an air layer between the body and the device. The respiratory sensing device 10 may detect respiration information as the respiratory sensing electrode is attached to the chest in a vertical direction, but the disclosure is not limited thereto, and the respiratory sensing electrode 10 may be attached at an appropriate attachment position considering the user's body structure. The appropriate attachment position may be a position where physical changes are noticeable according to breathing.

Additionally, the respiratory sensing device 10 further includes a first connection portion connected to other devices, and the respiratory sensing device 10 may be electrically connected, through the first connection portion, to an external electrocardiogram electrode, a temperature sensor, an acceleration sensor, a microphone, an electromyogram electrode, an electroencephalogram electrode, and the like. Through the first connection portion, an external electrocardiogram electrode, a temperature sensor, an acceleration sensor, a microphone, an electromyogram electrode, an electroencephalogram electrode, and the like may receive power from the respiratory sensing device 10 and transmit signals including measured measurement values to the respiratory sensing device 10.

The respiratory sensing device 10 may be attached to an attachment position for detecting respiration information and connected, through a cable, to another device attached to another position. The device, such as an electrocardiogram electrode, a temperature sensor, an acceleration sensor, a microphone, and the like, may be attached to a connection portion through a cable having a certain length. The respiratory sensing device 10 may receive an electrocardiogram signal from an electrocardiogram electrode. The respiratory sensing device 10 may receive a temperature value from a temperature sensor. The respiratory sensing device 10 may receive sensor values from an acceleration sensor, analyze the received sensor values, and calculate information such as motion values, orientation values, and impact values. The respiratory sensing device 10 may detect sudden movements such as falling or posture change through the information such as motion values, orientation values, and impact values. The respiratory sensing device 10 may receive a measurement value corresponding to a user's movement through an acceleration sensor. For example, an electrocardiogram electrode attached near the heart may be connected to the first connection portion through a separate cable. A microphone attached to measure sound may be connected to the first connection portion through a cable. The microphone may be attached around the user's nose or mouth to obtain respiration sound and transmit the obtained sound to the respiratory sensing device 10 through the first connection portion. The microphone may be attached to the back of a user to obtain sound of lung when breathing and transmit the sound to the respiratory sensing device 10 through the first connection portion. The respiratory sensing device 10 may obtain an electrocardiogram signal, a temperature signal, a sound signal, a movement signal, and the like, through other devices connected to the first connection portion. The external devices, such as an electrocardiogram electrode, a temperature sensor, an acceleration sensor, a microphone, and the like, may be connected to the respiratory sensing device 10 only when necessary, and may be detached when unnecessary.

The respiratory sensing device 10 according to embodiments may synchronize a respiration signal measured through a processing main board MB with an electrocardiogram signal, a temperature value, sound data, a movement value, and the like measured through other devices, by using a certain algorithm. The respiratory sensing device 10 may synchronize the electrocardiogram signal, temperature value, sound data, movement value, etc. based on the measured time value. The respiratory sensing device 10 may insert at least one of temperature value, sound data, and movement value to the ECG signal as a tag. The respiratory sensing device 10 may store the synchronized data in a memory.

Figure 1C:
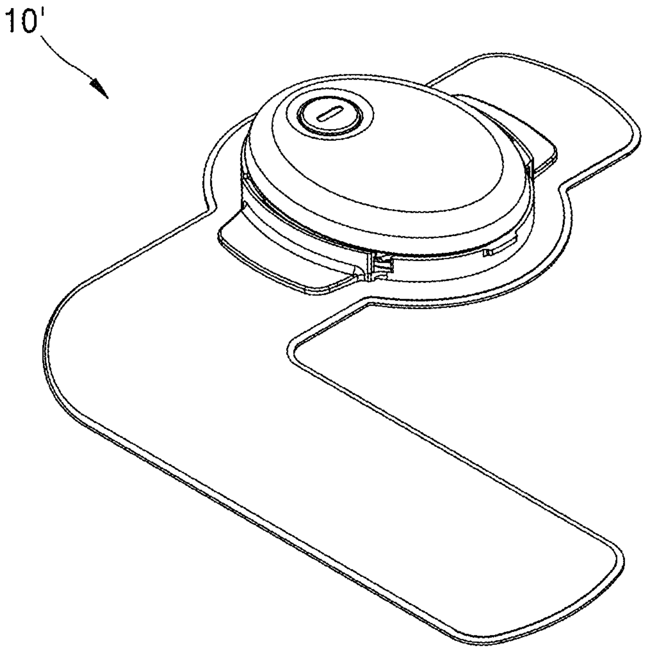
FIG. 1C is a perspective view of a respiratory sensing device according to another embodiment.

FIG. 1C is a perspective view of a respiratory sensing device 10' according to another embodiment. The respiratory sensing device 10' may have a shape bent at a certain angle. The respiratory sensing device 10' may be bent particularly by 90 degrees, but the disclosure is not limited thereto. The respiratory sensing device 10' may be bent at an angle of 45 degrees to 135 degrees. A main body portion and respiratory sensing electrodes may be located in opposite bent areas of the respiratory sensing device 10'.

Figure 2:
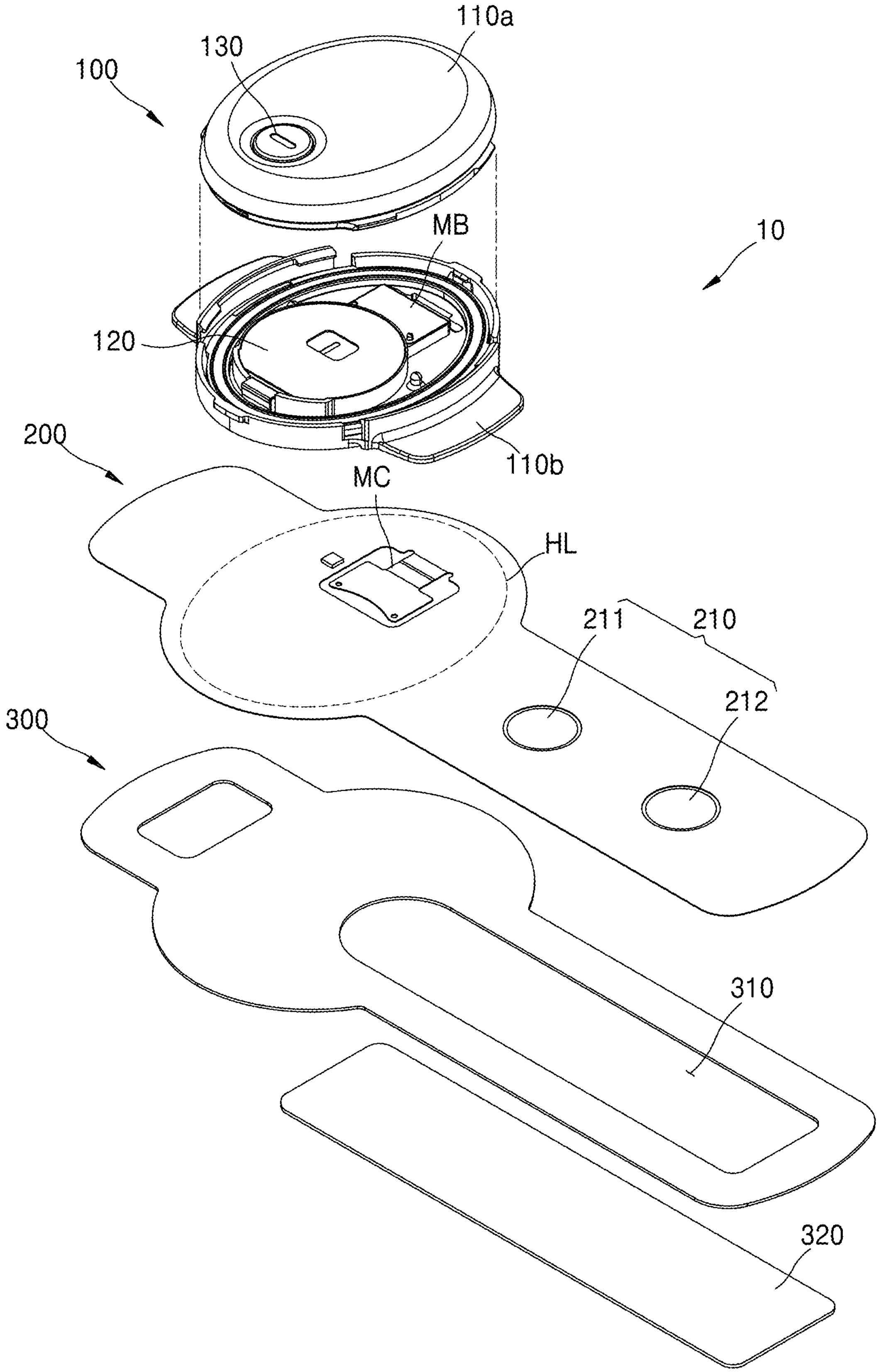
FIG. 2 is an exploded perspective view of a respiratory sensing device according to embodiments.

FIG. 2 is an exploded perspective view of the respiratory sensing device 10 according to embodiments. As illustrated in FIG. 2, the respiratory sensing device 10 may include a main body portion 100, a flexible substrate 200, and an adhesive member 300.

The main body portion 100 is disposed on a surface of the flexible substrate 200, and may include housings **110*a* and 110*b*, a battery 120**, a processing main board MB, memory, a connector MC, other support structures, and the like.

As illustrated in FIG. 1B, the housings 110_a_ and 110_b_ may be implemented as two separable structures. The housings 110_a_ and 110_b_ may be structures that can be assembled to each other. As the housings 110_a_ and 110_b_ are assembled to each other, other components of the main body portion 100 may be protected from external shocks and external foreign materials may not be introduced into the main body portion 100. The shape, size, and material of the housings 110_a_ and 110_b_ are not particularly limited, and may be appropriately selected according to the purpose of use of the respiratory sensing device 10, and the like. In an embodiment, the housings 110_a_ and 110_b_ may each have a dome shape having an inner space. A button 130 may be provided on upper surfaces of the housings 110_a_ and 110_b_. Although FIG. 1A illustrates that only one power button is provided on the upper surface of the housings 110_a_ the disclosure is not limited thereto. For example, a plurality of buttons to control power and an operating mode of the respiratory sensing device 10 may be provided on the upper surfaces or side surfaces of the housings 110_a_ and 110_b_. Here, the battery 120 provide power to a measuring component, which may be located inside the housing for a single-use or outside housing for easy-to-replace. The measuring component may include at least one of the processing main board MB, memory, and a connector MC. The battery 120 provide power to the measuring electronics, which may be located inside the housing for a single-use or outside housing for easy-to-replace.

The processing main board MB may be included in the main body portion 100, and the process MB controls a respiratory sensing electrode 210, the battery 120, and the like and processes a signal measured by the respiratory sensing electrode 210. The processing main board MB may receive signals and include a chip that processes signals and a communication module that receives signals through a network. The chip may amplify signals and convert analog signals into digital signals. The processing main board MB may receive the signal measured at the respiratory sensing electrode 210 and convert the signal into a digital signal. The communication module may transmit and receive signals using wireless or wired communication methods. The flexible substrate 200 may have a connector MC connected to the processing main board MB and transmit signals form the respiratory sensing electrode 210 and/or separate devices, such as an electrocardiogram electrode, a temperature sensor, a microphone, an acceleration sensor, and the like, to the processing main board MB trough an electric line. Furthermore, the main body portion 100 may include a memory to store a signal processing algorithm. The signals measured under the control of the processing main board MB may be stored in the memory.

The main body portion 100 may include a communication unit that transmits signals measured by the respiratory sensing electrode 210 and/or separate devices, such as an electrocardiogram electrode, a temperature sensor, a microphone, an acceleration sensor, and the like, to a monitoring device. The communication unit may include an identification (ID) for Bluetooth connection.

The main body portion 100 may include an alarm unit (not shown) that generates alarm signals, such as vibration, sound, and the like. The alarm unit may be controlled by the processing main board MB.

The flexible substrate 200 may include one or more respiratory sensing electrodes 210, a circuit electrically connected to the main body portion 100, and the like. The flexible substrate 200 may include in particular two or more respiratory sensing electrodes 210. The respiratory sensing electrode 210 may be provided avoiding an area HL where the main body portion 100 is arranged. The respiratory sensing electrode 210 may be provided in an area where the main body portion 100 is not located.

The flexible substrate 200 is in close contact with the user's body or skin, and a degrees of bending and the line may be changed according to a change in the body. One side of the flexible substrate 200, in which the main body portion 100 or the housing 110_a_, 110_b_ of a hard material is located, may not be freely bent along the body due to the main body portion 100 or the housing 110. The respiratory sensing electrode 210 may be provided avoiding an area where flexibility is lowered by the main body portion 100 or the housing 110_a_, 110_b_ of a hard material. The respiratory sensing electrode 210 may include respiratory sensing electrodes, for example, respiratory sensing electrodes 211 and 212 that are arranged in a row in the other side of the flexible substrate 200. As the respiratory sensing electrodes 211, 212 are arranged in a row, a change in capacitance values according to breathing may be measured. As the distance between the respiratory sensing electrodes 211 and 212 increases, an air layer between the respiratory sensing electrode and the skin may increase. As the respiratory sensing electrodes 210 are arranged in a row, the respiratory sensing electrodes 210 may well detect a change in the air layer due to expansion or contraction of the body according to a respiration cycle. The respiratory sensing electrodes 210 are arranged apart from each other by a certain distance or more. In particular, the certain distance may be 0.5 cm or more. The respiratory sensing electrodes 210 may include two or more respiratory sensing electrodes. As the number of the respiratory sensing electrodes 210 increases, a change in the air layer according to breathing may be further well detected.

The flexible substrate 200 may have a strip shape elongated in the horizontal direction in which the respiratory sensing electrode 210 is arranged. The length in the horizontal direction may be set to a set multiple or more of the length in the vertical direction. In another embodiment, the flexible substrate 200 may have a strip shape bent at a certain angle. In this case, the respiratory sensing electrode 210 and the main body portion 100 are provided at opposite sides so as not to be adjacent to each other, and thus, an area where the respiratory sensing electrode 210 is located and an area where the main body portion 100 is located may form a certain angle.

When the respiratory sensing electrodes 210 are arranged to overlap or to be adjacent to the main body portion 100, flexibility is lowered by the main body portion 100 so that a change depending on the body change may be difficult to sense. Accordingly, the respiratory sensing electrodes 210 may be spaced apart from each other by a certain distance or more. In another embodiment, when the material of the main body portion 100 is flexible, the respiratory sensing electrode 210 may be arrange to overall or to be adjacent to the main body portion 100.

The respiratory sensing electrode 210 may be designed to be disposed on the flexible substrate 200 to have a sensing value varying depending on a change in the air layer. The flexible substrate 200 may have a shape elongated in a direction in which the respiratory sensing electrodes 210 are provided. The respiratory sensing electrode 210 may measure capacitance values varying depending on a respiration cycle. A degree of a change in the capacitance value measured by the respiratory sensing electrode 210 may vary depending on the position and/or an object to which the respiratory sensing electrode 210 is attached. An expiration time point, an inspiration time point, and the like of respiration may be determined based on the signal measured by the respiratory sensing electrode 210.

The adhesive member 300 is provided at the other surface of the flexible substrate 200 so that the respiratory sensing device 10 may be attached to the user's body. The adhesive member 300 is coated with an adhesive material to allow the flexible substrate 200 to be attached to the skin. The adhesive member 300 may include a double-sided tape, a silicon tape, and the like, but the disclosure is not limited thereto, and the adhesive member 300 may be implemented with various adhesive materials. The adhesive member 300 may include an opening portion 310 at a position corresponding to the respiratory sensing electrode 210. The respiratory sensing electrode 210 may be exposed to the outside through the opening portion 310 while not attached to the body. Although the opening portion 310 may be implemented as a hole shape, the opening portion 310 may be changed into various shapes to expose the respiratory sensing electrode 210 to the outside.

A cover member 320 may be further provided on the other surface of the adhesive member 300. The cover member 320 may be implemented with a flexible material. The cover member 320 may include a hole through which air passes. The cover member 320 may be implemented with a material being flexible and air-permeable. The cover member 320 may cover the opening portion 310 of the adhesive member 300. The cover member 320 may be implemented to cover a part or whole of the adhesive member 300 or a part of whole of the opening portion 310. The cover member 320 may be coated with an adhesive material to allow the respiratory sensing device 10 to be well attached to the skin. The cover member 320 may be removed before used for respiratory sensing. The cover member 320 may be implemented with a high dielectric elastic material.

Figure 3:
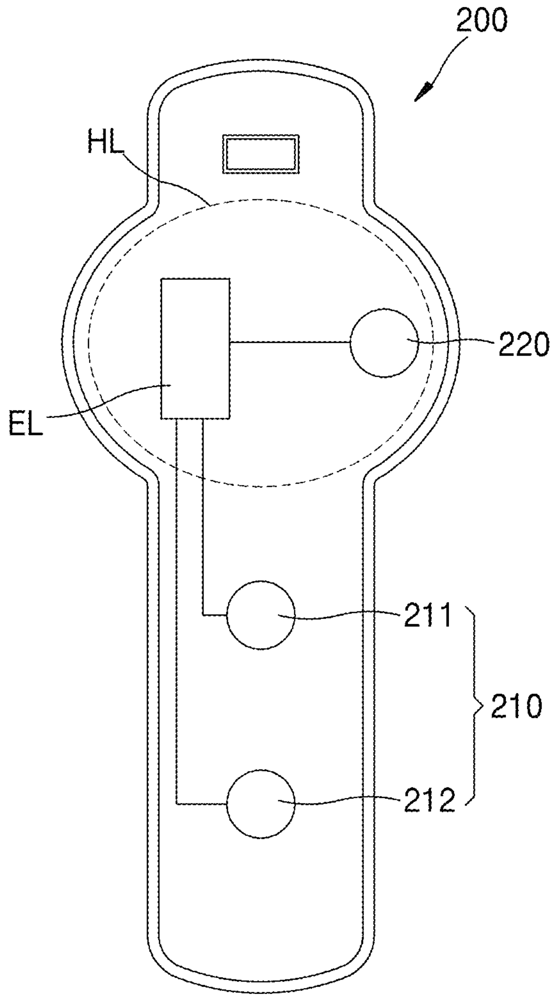
FIG. 3 is a bottom view of a flexible substrate according to embodiments.

FIG. 3 is a bottom view of the flexible substrate 200 according to embodiments. As illustrated in FIG. 3, the flexible substrate 200 may further include an electrocardiogram electrode 220. The electrocardiogram electrode 220 may be located within the area HL where the main body portion 100 is located, on the flexible substrate 200. The adhesive member 300 may further include a conductive hole that is electrically connected to the skin in an area in contact with the electrocardiogram electrode 220. The conductive hole may be formed by penetrating the adhesive member 300. The conductive hole may be filled with a conductive material, such as hydrogel and the like. The flexible substrate 200 may further include an electrical line EL through which electrical signals from the respiratory sensing electrodes 211 and 212 and the electrocardiogram electrode 220 are transmitted. In another embodiment, the flexible substrate 200 may further include electrical lines electrically connected to a first connection portion (230 in FIG. 5A) and a second connection portion (240 in FIG. 5C).

In another embodiment, the electrocardiogram electrode 220 may be implemented to be provided in separate devices to be connected to the respiratory sensing device 10 through the first connection portion 240. When the measurement of an electrocardiogram signal is unnecessary, the electrocardiogram electrode 220 may be detached. The electrocardiogram electrode 220 may be attached to an attachment position where electrocardiogram measurement is available. In particular, the electrocardiogram electrode 220 may be attached to the skin over the ribs under the left chest at a level similar to the lungs. The electrocardiogram electrode 220 is connected to the respiratory sensing device 10 through a cable to measure an electrocardiogram signal by the control of the respiratory sensing device 10. The electrocardiogram electrode 220 may transmit the measured electrocardiogram signal to the main body portion 100 of the respiratory sensing device 10.

The electrocardiogram electrode 220 may be arranged in the area HL that is one side of the flexible substrate 200 and in which the main body portion 100 is located, and the respiratory sensing electrode 210 may be arranged in an area other than the area HL in the other side. The respiratory sensing electrode 210 and/or the electrocardiogram electrode 220 may be electrically connected to the main body portion 100 to receive power and transmit the measured signal.

Figure 4:
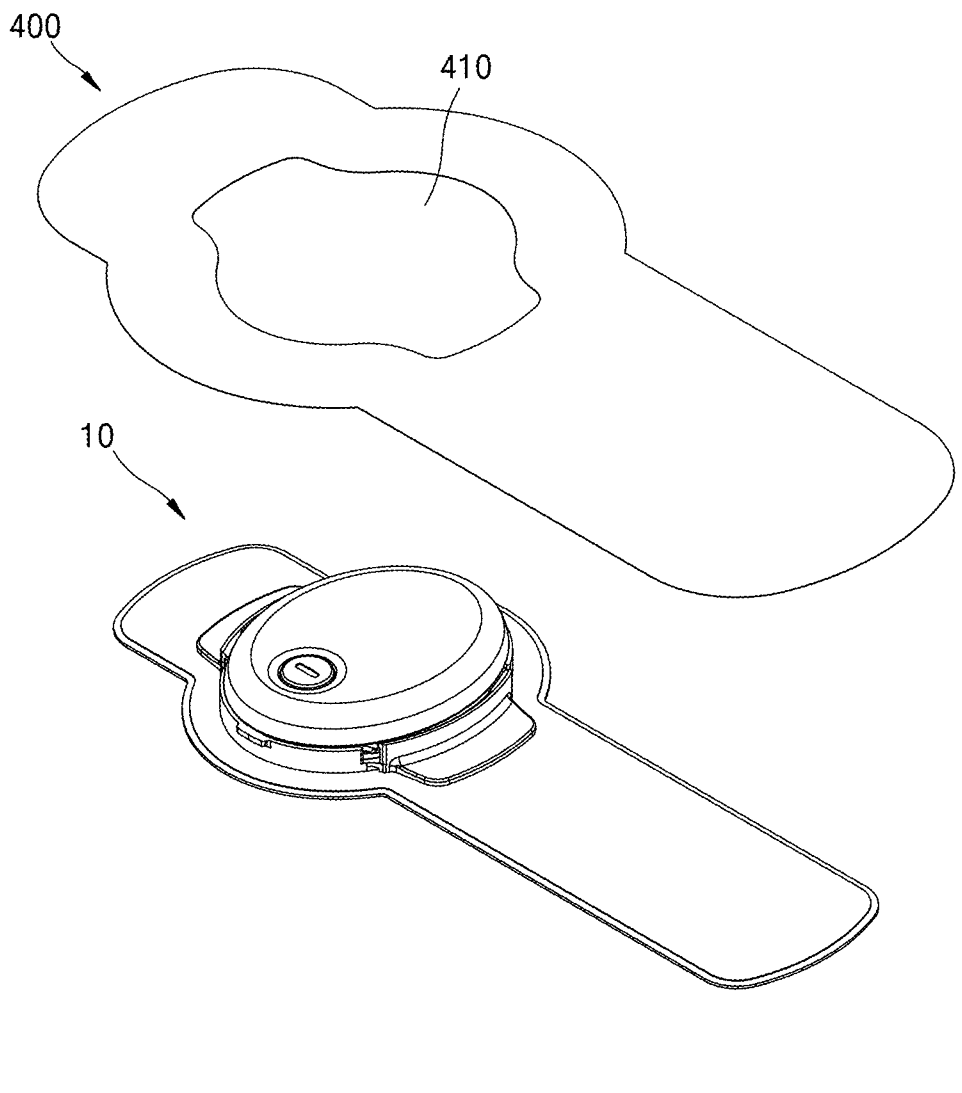
FIG. 4 is a perspective view of a respiratory sensing device with a protection member.

FIG. 4 is a perspective view of the respiratory sensing device 10 with a protection member 400.

As illustrated in FIG. 4, the respiratory sensing device 10 may further include the protection member 400. The protection member 400, as a device to protect the flexible substrate 200, may be implemented with a waterproof material. The protection member 400 may be implemented with a polyurethane (PU) material. The protection member 400 may have a shape corresponding to the flexible substrate 200, but the disclosure is not limited thereto, and the protection member 400 may have various shapes. The protection member 400 may be implemented to be greater than the flexible substrate 200 to cover the flexible substrate 200. The protection member 400 may further include an opening portion 410 that exposes the main body portion 100 not to cover the main body portion 100. The opening portion 410 may have a shape corresponding to the main body portion 100.

Figure 5A:
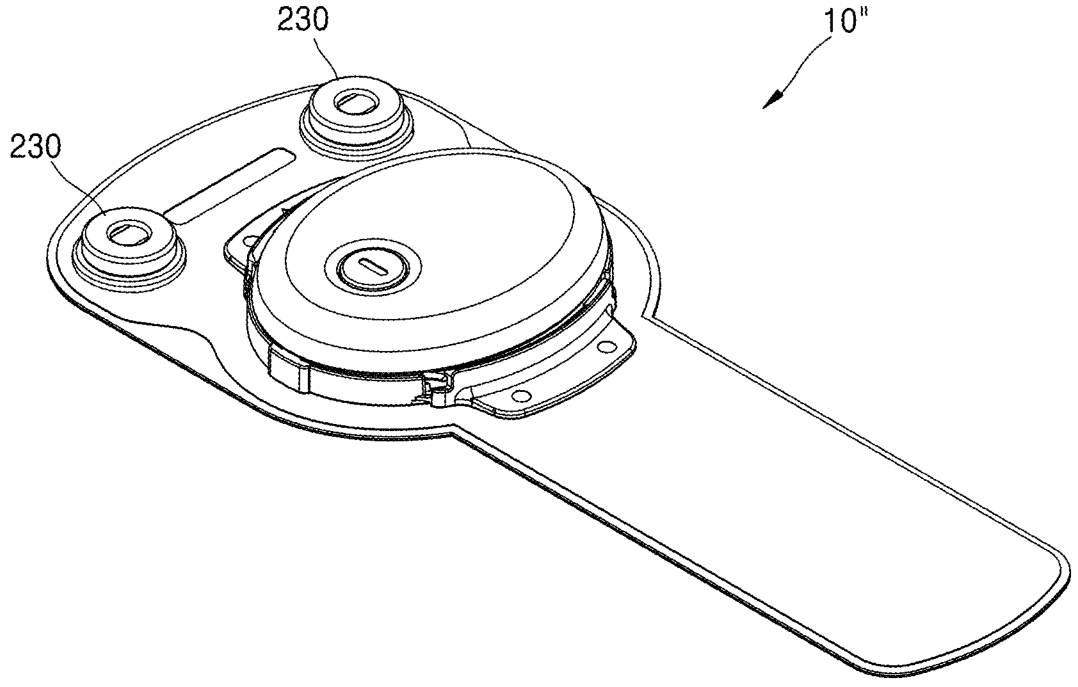
FIG. 5A is a perspective view of a respiratory sensing device including a first connection portion, according to some embodiments.

FIG. 5A is a perspective view of a respiratory sensing device 10" with the first connection portion 230, according to some embodiments. As illustrated in FIG. 5A, the respiratory sensing device 10" may further include the first connection portion 230 connected to other devices, such as an electrocardiogram sensor device, a temperature sensor, a sound sensor, and the like. The first connection portion 230, which is electrically connected to other devices, may supply power to the other devices and receive signals measured by the other devices. The first connection portion 230 may transmit an operation signal to the other devices. Although two first connection portions 230 are illustrated in FIG. 5A, by way of example, two or more first connection portions 230 may be provided. The first connection portion 230 may be provided in one side of the flexible substrate 200, but the disclosure is not limited thereto, and the first connection portion 230 may be provided in one side of the main body portion 100. The first connection portion 230 may be configured to be connected to the processing main board MB of the main body portion 100 by an electrical wire and to be connectable with other devices. The first connection portion 230 may be implemented as a snap fastener and the like to be structurally coupled to other devices. The other devices may be attached to the first connection portion 230 through a cable and the like connected to the first connection portion 230. The length of the cable may be changeable. When the first connection portion 230 is determined to be connected to another device, the processing main board MB of the main body portion 100 may receive and process a signal from the device.

Figure 5B:
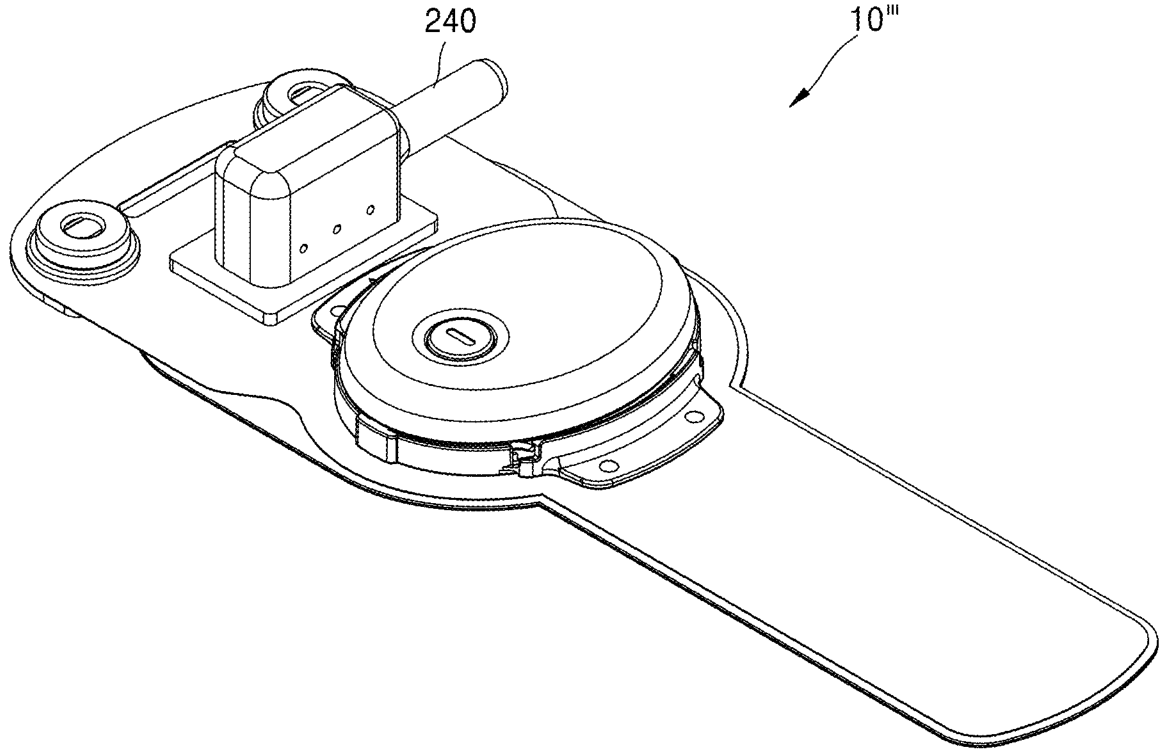
FIG. 5B is a perspective view of a respiratory sensing device including a second connection portion, according to some embodiments.

FIG. 5B is a perspective view of a respiratory sensing device 10" with the second connector 240, according to some embodiments.

Figure 5C:
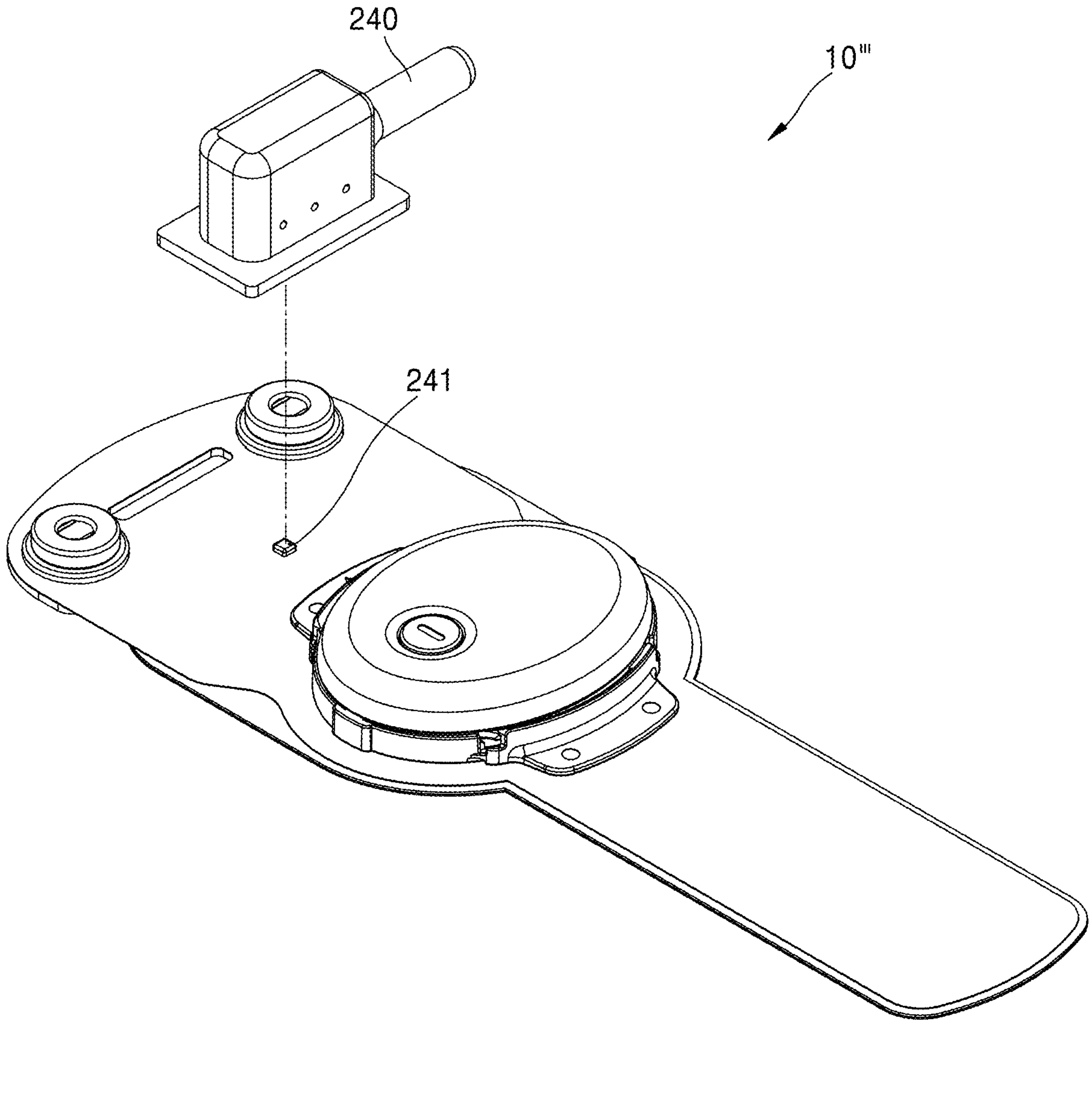
FIG. 5C illustrates the interior of the second connection portion of the respiratory sensing device of FIG. 5B.

As illustrated in FIG. 5B, the respiratory sensing device 10" may further include the second connector 240 connected to a nasal breathing device. The nasal breathing device, as illustrated in FIG. 10B, is a device attached to the user's nose to collect and move air generated from the nose, and may include a collection device attached to the nose to collect air generated from the nose, a tube to move the air collected by the collection device, and a band to allow the device to be in close contact with the use's face. The respiratory sensing device 10" may include the second connector 240 without the first connection portion 230. The second connector 240 may include a pressure sensor connected to the tube of the nasal breathing device (20 in FIG. 10B) to measure the flow of air discharged by the nasal breathing. As shown in FIG. 5C, the respiratory sensing device 10" may further include a pressure sensor 241. The pressure sensor 241 may measure the pressure value of air discharged from the nose through the second connector. When the pressure value is a reference pressure value or more (exceed), it may be determined that nasal breathing has occurred. Here, the reference pressure value may be determined or set differently for each user. The reference pressure value may be determined based on values measured for the user. The value measured by the pressure sensor 241 may be transmitted to the processing main board MB of the main body portion 100. The processing main board MB of the respiratory sensing device 10" may determine that there is nasal breathing when the pressure measured by the pressure sensor 241 exceeds a preset reference pressure value, which means that there is air discharged from the nose. The respiratory sensing device 10" may detect that nasal breathing has occurred through a time point when the pressure measured by the pressure sensor 241 increases. Furthermore, the respiratory sensing device 10" may detect the time point when the pressure measured by the pressure sensor 241 increases, as a time point when the nasal breathing starts.

Figure 6:
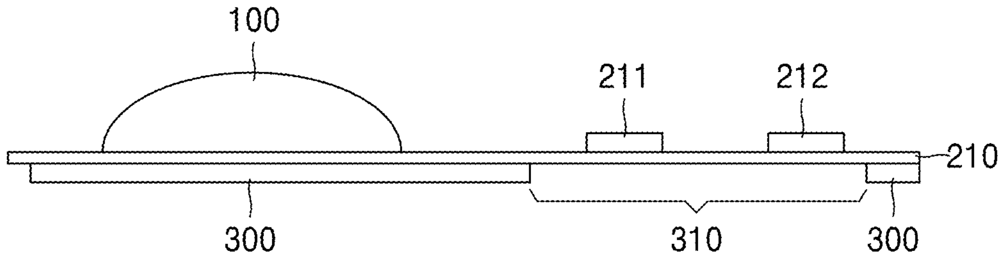
FIG. 6 is a cross-sectional view of the respiratory sensing device taken along a line II-II of FIG. 1A.

FIG. 6 is a cross-sectional view of the respiratory sensing device 10 taken along a line II-II of FIG. 1A. The main body portion 100 may be disposed on one surface of the flexible substrate 200, and the respiratory sensing electrodes 211 and 212 may be disposed on the same surface. In a selective embodiment, the respiratory sensing electrodes 211 and 212 may be provided in such a manner of being included in the flexible substrate 200. The respiratory sensing electrodes 211 and 212 may be spaced apart from each other by a certain distance. The adhesive member 300 is disposed on the other surface of the flexible substrate 200, in a part of an area excluding a position corresponding to the respiratory sensing electrodes 211 and 212, so that the respiratory sensing electrodes 211 and 212 may be exposed to the outside. The respiratory sensing electrodes 211 and 212 are arranged apart from the skin by a certain distance through the adhesive member 300 and the opening portion 310. The opening portion 310 may be implemented in singular or plural form. As the respiratory sensing electrodes 211 and 212 are apart from the skin, a certain air layer exists between the respiratory sensing electrode 210 and the skin.

Figure 7A:
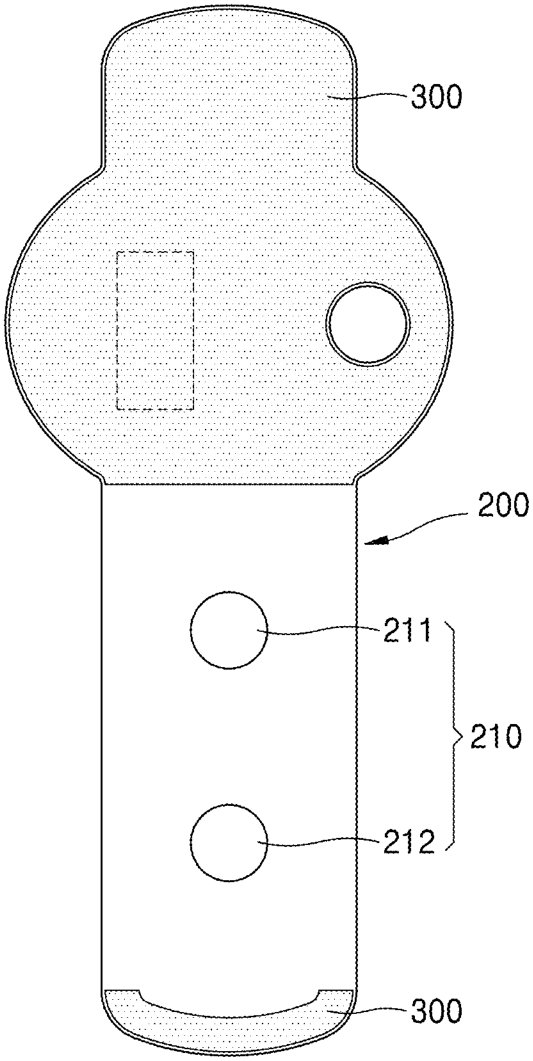
Figure 7B:
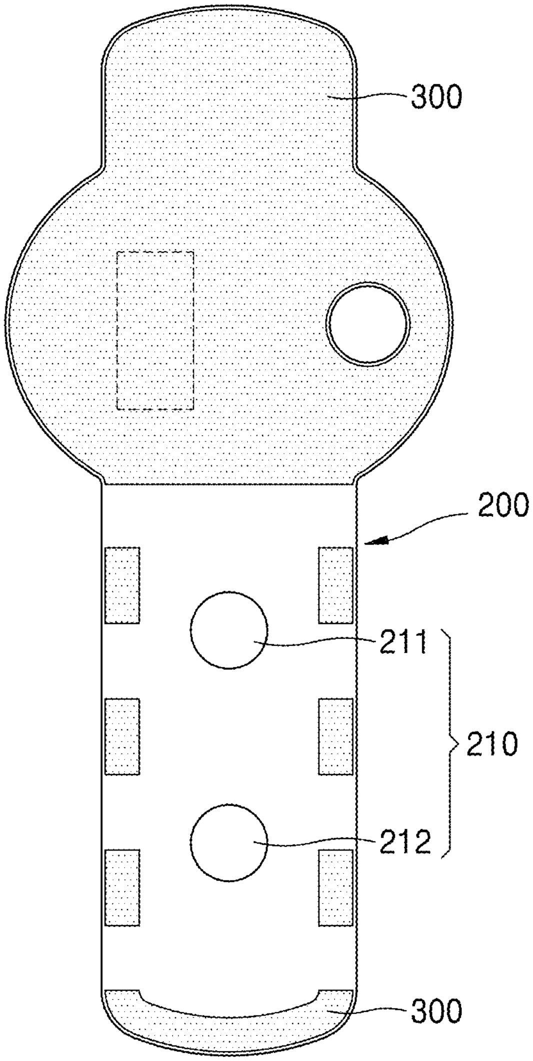
Figure 7C:
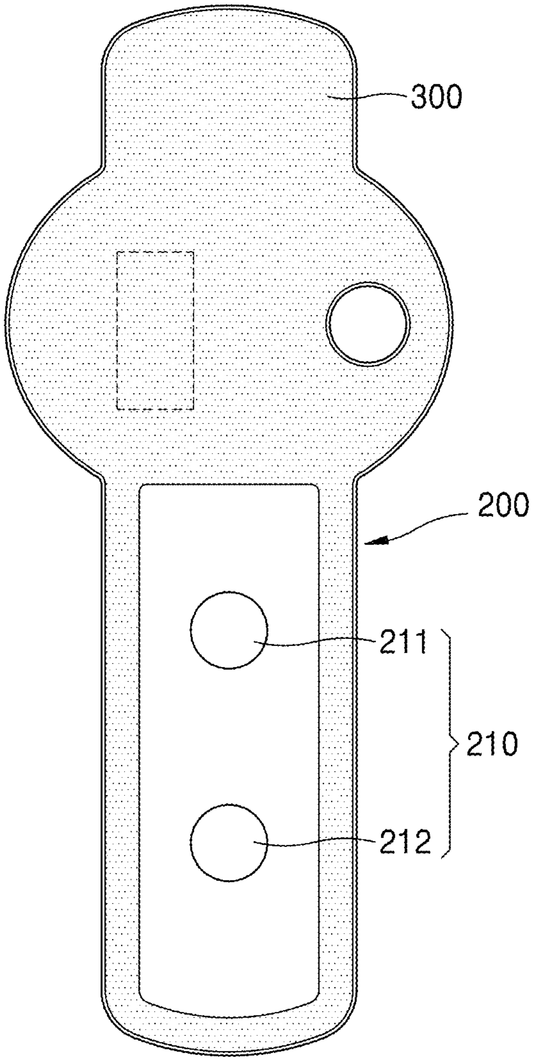

FIG. 7A illustrates a first embodiment of an adhesive member 300. FIG. 7B illustrates a second embodiment of an adhesive member 300. FIG. 7C illustrates a third embodiment of an adhesive member 300.

The adhesive member 300 may be implemented in a shape exposing the respiratory sensing electrode 210. The adhesive member 300 may be modified in various ways as long as the adhesive member 300 has a shape that exposes the respiratory sensing electrode 210. The adhesive member 300 may be implemented to have a single region or multiple regions that is separated with respect to the respiratory sensing electrodes 211 and 212.

As illustrated in FIG. 7A, the adhesive member 300 may be separated into two parts and arranged in an area where the main body portion 100 is located and an area where the respiratory sensing electrode 210 does not exist. As illustrated in FIG. 7B, the adhesive member 300 may be separated into a plurality of parts to have a shape arranged at a position surrounding the respiratory sensing electrode 210 while avoiding a position corresponding to the respiratory sensing electrode 210. As illustrated in FIG. 7C, the adhesive member 300 may be implemented in a shape including an opening portion corresponding to the respiratory sensing electrode 210. The adhesive member 300 is not limited to the illustrations in the drawings, and may be implemented to cover a part or whole of the area of the flexible substrate 200 excluding the respiratory sensing electrode 210.

Figure 8:
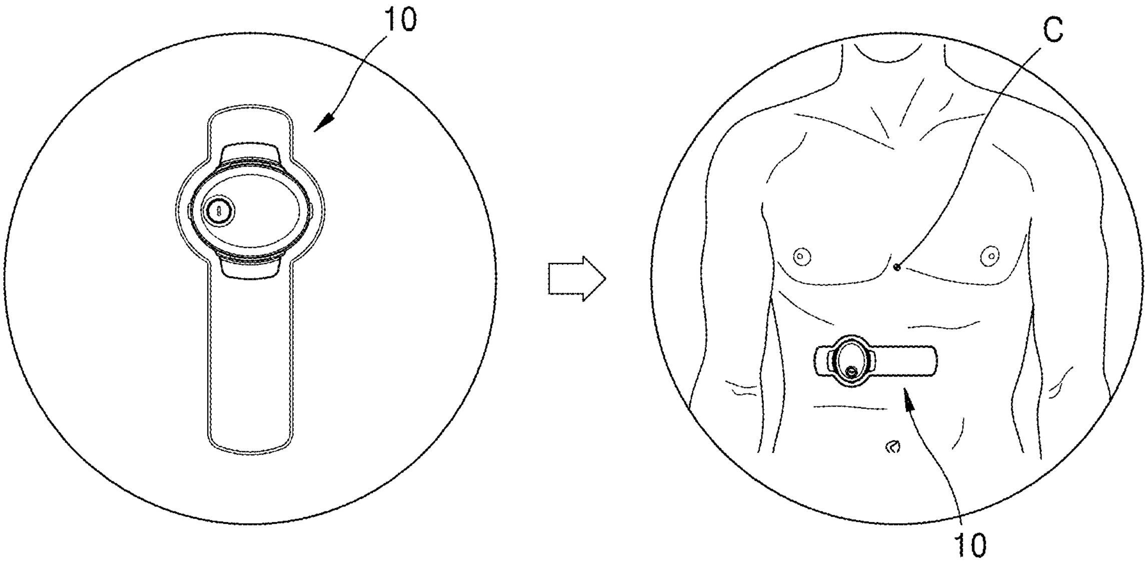
FIG. 8 illustrates a method of using a respiratory sensing device, according to embodiments.

FIG. 8 illustrates a method of using the respiratory sensing device 10, according to embodiments. Referring to FIG. 8, a user may check an attachment area before wearing the respiratory sensing device 10. The attachment area is an area that expands or contracts by a flow of air through breathing, which may be an abdomen or chest portion, but the disclosure is not limited thereto, and an area in which a change in a respiration process is substantial may be determined as the attachment area. In the respiratory sensing device 10, one side where the respiratory sensing electrode 210 is located may be attached to face a center C of the chest or abdomen. When there is a lot of hair in the attachment area, the hair may be removed using a shaver. The attachment area may be cleaned using an alcohol swab, and then sufficiently dried one minute or more after cleaning.

Next, a transfer film adhering on the respiratory sensing device 10 is removed, and the respiratory sensing device 10 is attached to the attachment area such that the respiratory sensing electrode 210 is located in the attachment area. In this case, the whole portion of the respiratory sensing device 10 is uniformly pressed for one minute or more so that the respiratory sensing device 10 may be well attached thereto. Then, a battery is electrically connected to the respiratory sensing device 10, and the respiratory sensing device 10 is connected to a device, such as a smartphone and the like, capable of monitoring and controlling and checks a respiration signal and the like. The connection to a device, such as a smartphone and the like, may use a Bluetooth method, but the disclosure is not limited thereto, and various wireless communications may be used therefor.

Figure 9:
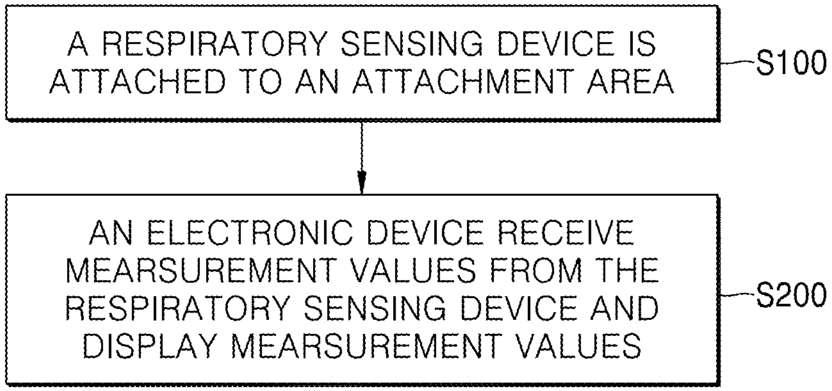
FIG. 9 is a flowchart of a method of using a respiratory sensing device, according to embodiments.

FIG. 9 is a flowchart of a method of using the respiratory sensing device 10, according to embodiments. Referring to FIG. 9, in S100, a transfer film is removed from the respiratory sensing device 10, and the respiratory sensing device 10 is attached to an attachment area. The attachment area may be a part of the user's body. The area of attachment may be any area adjacent to the abdomen or chest. The attachment area may be an area determined by the medical staff. In the respiratory sensing device 10, one side where the respiratory sensing electrode 210 is arranged may be attached to face the center of the chest or abdomen. In the body, a portion that is expands or contracts according to breathing may be determined as the attachment area. Shaving and alcohol disinfection may be performed, if necessary, before attaching the respiratory sensing device 10. After attaching the respiratory sensing device 10, the whole portion may be uniformly pressed for one minute or more.

In S200, an electronic device that wirelessly communicates with the respiratory sensing device 10 may receive measurement values and display the measurement values. The electronic device may refer to a computing device including at least one processor, the communication interface, and a display device. The electronic device may display the measurement value. The measured value may include at least one of a respiration signal, an electrocardiogram signal, a temperature signal, a sound signal, and a movement value. The electronic device may calculate a value related to whether the user is apnea based on the measured values. The device may calculate and display information related to the user's apnea, for example, apnea time period, apnea time point, etc. Through the displayed measurement value on the electronic device, a user may determine whether the measurement values match the user's respiration, that is, whether a capacitance value that varies according to the user's breathing has been measured. When the measurement value does not match the user's breathing, the attachment position of the respiratory sensing device 10 may be changed. The user may check again, through the electronic device, a measurement value measured by the respiratory sensing device 10 attached to a changed attachment position.

In the description of FIG. 9, the respiratory sensing device 10 may be replaceable with the respiratory sensing devices 10', 10", and 10".

Figure 10A:
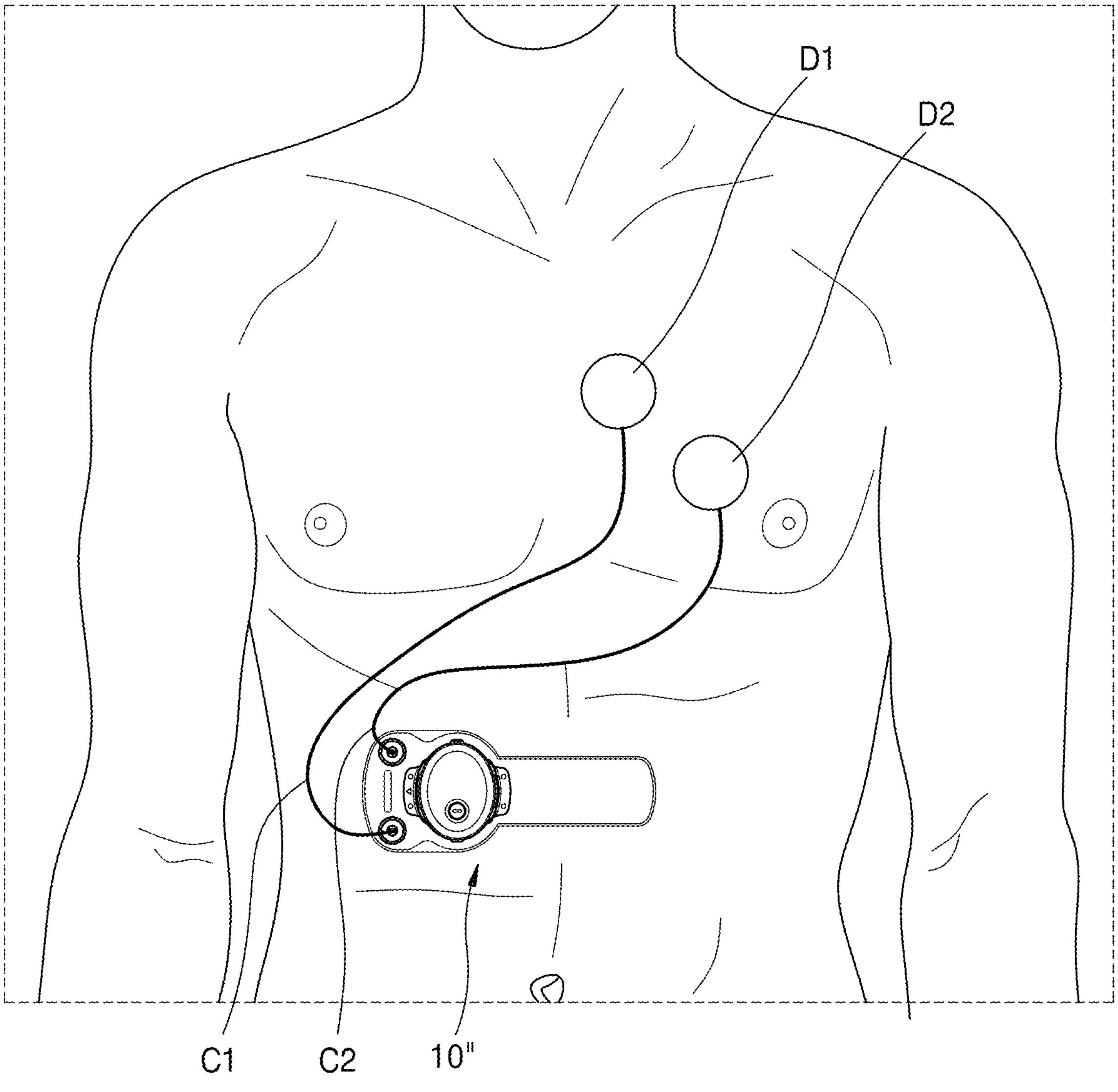
FIG. 10A illustrates an example of attaching a respiratory sensing device including a first connection portion to the body, according to embodiments.
Figure 10B:
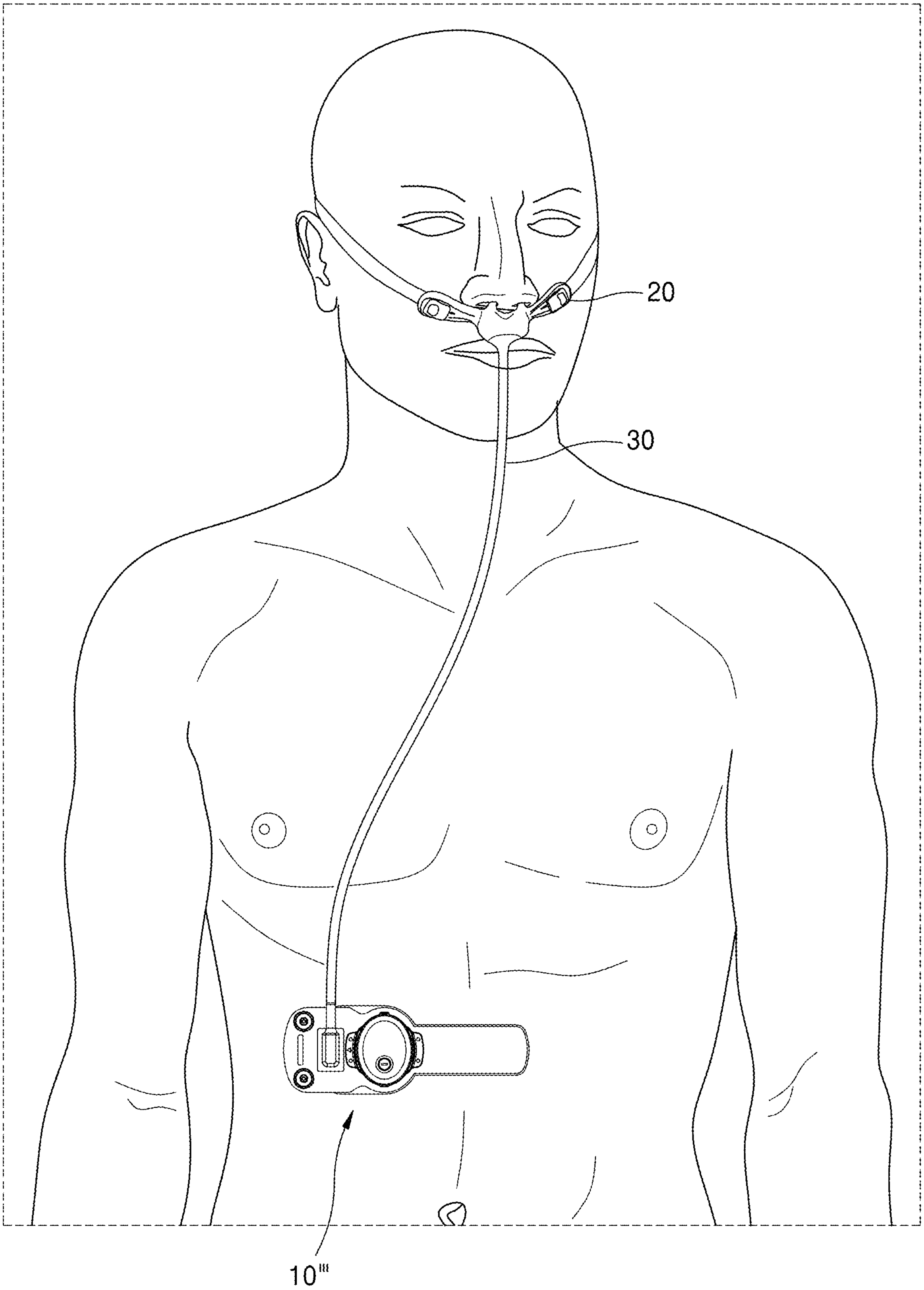
FIG. 10B illustrates an example of attaching a respiratory sensing device including a second connection portion to the body, according to embodiments.

FIG. 10A illustrates an example of attaching a respiratory sensing device including a first connection portion to the body, according to embodiments.

The respiratory sensing device 10" may be attached, in a horizontal direction, to a portion around the abdomen where a change according to breathing is detected. The respiratory sensing device 10" may be connected to separate devices D1 and D2 through cables C1 and C2. The separate devices D1 and D2 may include at least one of an electrocardiogram electrode, a temperature sensor, a microphone, and an acceleration sensor. The respiratory sensing device 10" may measure temperature values, such as the user's body temperature, ambient temperature, and the like by additionally connecting a temperature sensor. The respiratory sensing device 10" may measure breathing sound, auscultation sound, the user's voice, snoring sound, and the like by additionally connecting a microphone. The respiratory sensing device 10" may measure the user's movement value, and the like by additionally connecting an acceleration sensor. The respiratory sensing device 10" may measure an electrocardiogram signal by additionally connecting an electrocardiogram electrode. The respiratory sensing device 10" may generate synchronized data by corresponding the signal measured by the respiratory sensing electrode 210 and the signals measured by the separate devices to a measurement time, and store such data. The respiratory sensing device 10" may transmit the measured signals and/or the synchronized data to the monitoring device through the communication unit.

FIG. 10B illustrates an example of attaching the respiratory sensing device 10" with the second connection portion 240 to the body, according to embodiments. The respiratory sensing device 10' may be attached to the body and may sense a change in the capacitance value according to breathing. The second connection portion 240 of the respiratory sensing device 10" may be connected to a tube 30 of a user's nasal breathing device 20. Air discharged from the nose may be moved to the second connection portion 240 through the tube 30. A large amount of air discharged from the nose may increase the pressure value of the pressure sensor 241. Whether air is discharged from the nose may be determined by measuring the pressure value. When the pressure value of the pressure sensor increases above (exceeds) the reference pressure value by the air from the nose, it is detected that nasal breathing is made. A time point of increase in the pressure value may be determined as a time point of nasal breathing. The respiratory sensing device 10" may determine whether nasal breathing occurs without omission at the time of respiration, by determining whether to breathe through the breathing sensing electrode and whether to breathe through the nose through the pressure value of the pressure sensor 241. It may be determine whether the time point of nasal breathing and the time point of lung breathing are synchronized with each other. As nasal breathing is made corresponding to the expiration point of respiration, an increase of the pressure value of the pressure sensor 241 may be detected. In this connection, it may be detected that, at the expiration point through the respiratory sensing electrode 210, the pressure value of the pressure sensor 241 increases above (e.g., exceeds) the reference pressure value. When an increase in the pressure value is detected, it may be determined that nasal breathing has occurred. When at the expiration point through the respiratory sensing electrode 210, the pressure value of the pressure sensor 241 does not increase above (e.g., exceeds) the reference pressure value, it may be determined that nasal breathing has not occurred. When the pressure value of the pressure sensor 241 increases above the reference pressure value at a time point later than the expiration point determined through the respiratory sensing electrode 210, it may be determined that nasal breathing occurs after lung breathing. As described above, the respiratory sensing devices 10, 10", 10'" can determine whether a person is breathing through the nose.

Figure 11A:
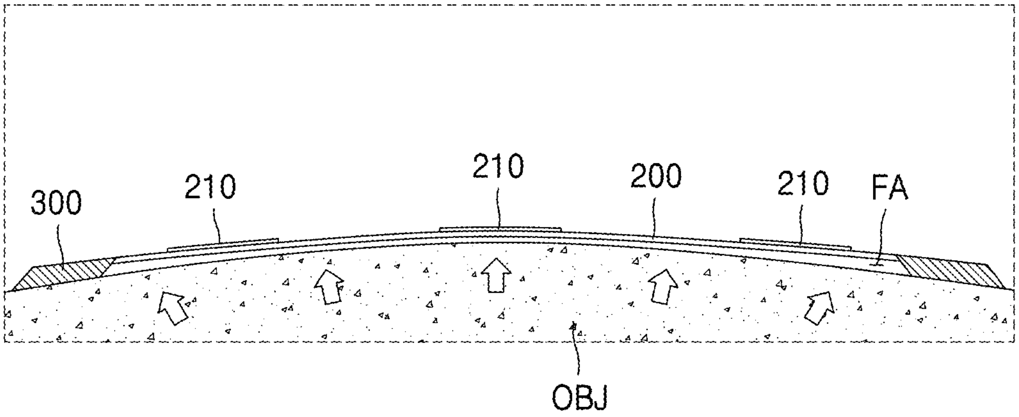
Figure 11B:
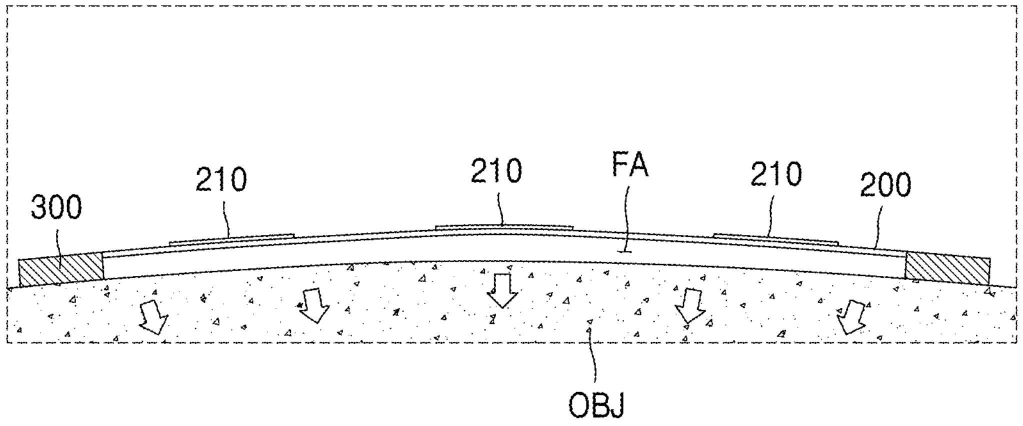

FIGS. 11A and 11B illustrate a change of an air layer in the respiratory sensing device 210 according to a respiration cycle.

As illustrated in FIG. 11A, at the inspiration phase of respiration, as the abdomen expands, the air layer formed corresponding to the respiratory sensing electrode 210 contracts, and thus, the value of capacitance measured by the respiratory sensing electrode 210 is changed. As illustrated in FIG. 11B, at the expiration phase of respiration, as the abdomen contracts, the air layer formed corresponding to the respiratory sensing electrode 210 increases, and thus, the value of capacitance measured by the respiratory sensing electrode 210 is changed.

According to any one of the embodiments described above, a change in capacitance due to expansion or contraction of the abdomen, the chest, or the like according to breathing may be detected using a structure that is attached to the user's skin and includes an air layer between the skin and a respiratory sensing electrode, and whether to breathe, a breathing time, and the like may be sensed depending on the capacitance change pattern. The air layer may be replaced with a high dielectric elastic layer. The high dielectric elastic layer can prevent from moisture stacking between the respiratory sensing electrode and skin.

Figure 12A:
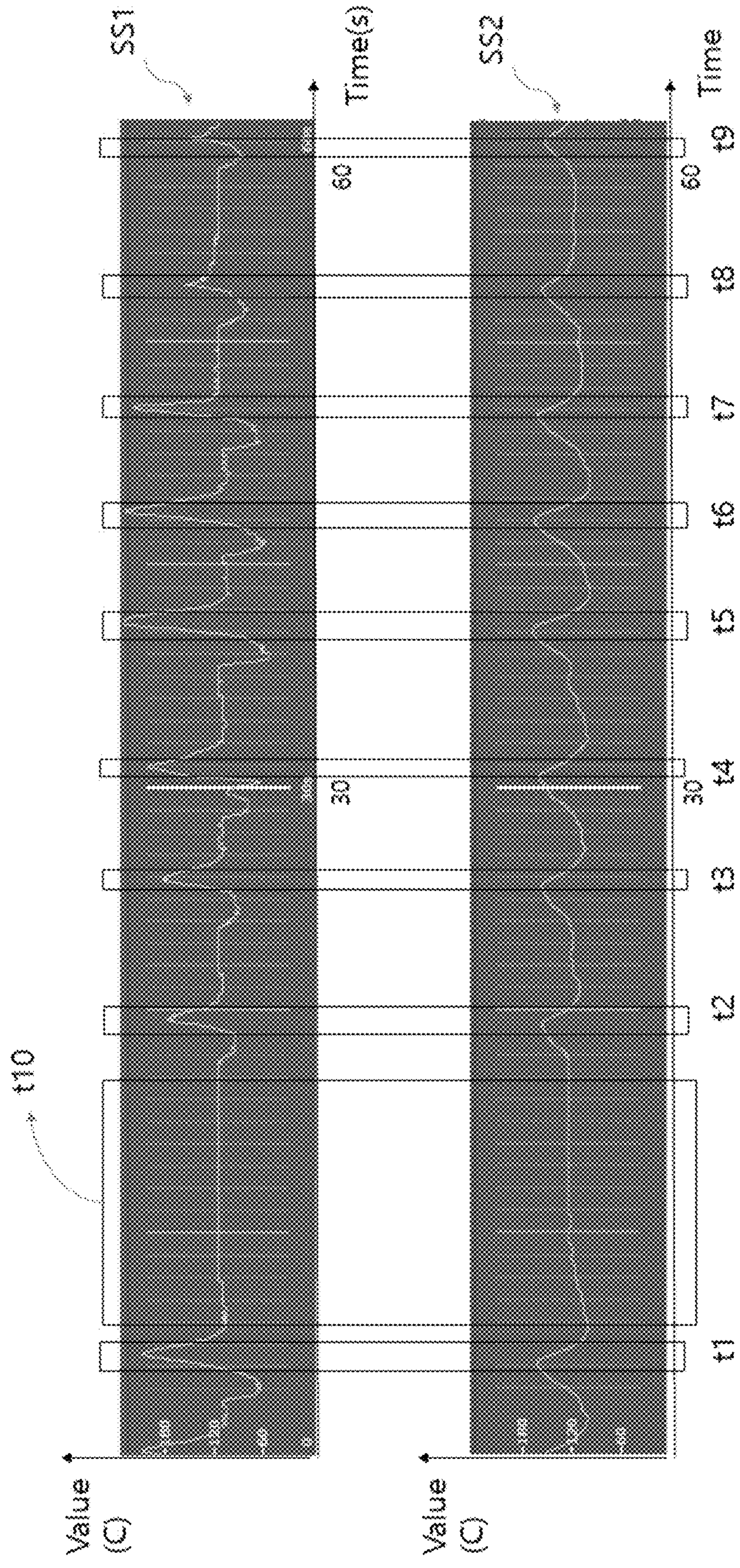
FIG. 12A is an example diagram of a first signal measured by a respiratory sensing electrode and a second signal measured by the respiratory sensing electrode, according to embodiments.

FIG. 12A is an example diagram of a first signal measured by the respiratory sensing electrode 211 and a second signal measured by the respiratory sensing electrode 212 according to embodiments.

The first signal and the second signal may be converted into a graph of change in capacitance value C over time and stored. The first and second signals may have increased values in the breath-in time period and may have decreased values in the breath-out time period. The values of the first and second signals may be measured to have stable values during an apnea period.

The respiratory sensing device 10 may detect, in the first and second signals, a first time period in which the slope value with respect to time is positive (>0) and a second time period in which the slope value is negative (<0). The respiratory sensing device 10 may detect the first time period as inspiration and the second time period as expiration. The respiratory sensing device 10 may determine a third time period in which the slope value is close to 0 as the apnea period.

In another embodiment, a time period with a value greater than a first reference value may be detected as the first time period, and a time period with a value less than a second reference value may be detected as the second time period. The respiratory sensing device 10 may determine the third time period having a slope between the first reference value and the second reference value as the apnea state. Here, the first reference value may be a positive number, and the second reference value may be a negative number.

The respiratory sensing device 10 may calculate time periods t1, t2, t3, t4, t5, t6, t7, t8, and t9 generated by the intersection of the first time period and the second time period. The breathing sensing device 10 calculates the user's breathing time interval based on the average time value in the time periods t1, t2, t3, t4, t5, 6, t7, t8, and t9.

User's breathing time interval=$(t9-t1)$/number of breaths (8)

In another embodiment, the user's breathing time interval may be a value calculated through a normal breathing signal measured from the user. The breathing sensing device 10 may determine the time interval t10 between t1 and t2, which has a longer breathing time interval, as the apnea time interval, compared with the user's breathing time interval.

Figure 12B:
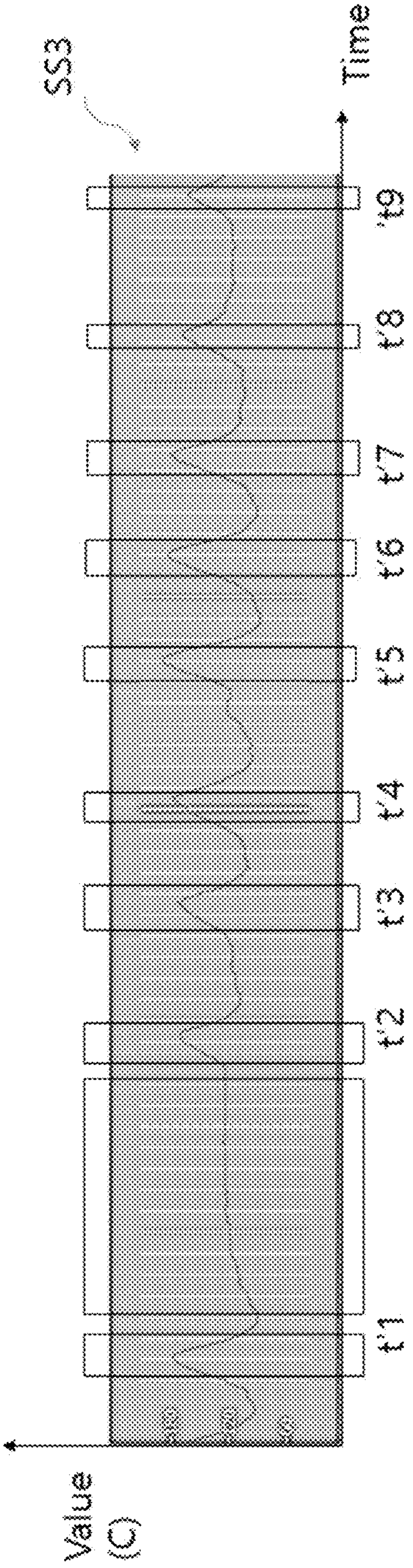
FIG. 12B is an example diagram of a third signal measured by the pressure sensor, according to embodiments.

FIG. 12B is an example diagram of a third signal SS3 measured by the pressure sensor 241 according to embodiments. The respiratory sensing device 10''' may acquire the third signal SS3 measured by the pressure sensor 241. The third signal SS3 may be a signal measuring the pressure of air discharged from the nose. As shown in FIG. 12B, the pressure sensor 241 may measure the value to increase when air is inhaled through the nose. Conversely, the pressure sensor 241 may measure the value to decrease when air is inhaled through the nose.

The respiratory sensing device 10''' may determine the time section including the time point at which the value increases and then decreases in the third signal as the respiration point. The respiratory sensing device 10''' is a time interval t'1, t'2, t'3, t'4, t'5, t'6, t'7, t'8, t'9 including the time point at which the value increases and then decreases in the third signal. The breathing sensing device 10''' may set a median values (average values) of the time intervals t'1, t'2, t'3, t'4, t'5, t'6, t'7, t'8, and t'9 as the breathing point values. The breathing sensing device 10''' may calculate the interval between respiration timing values as the respiration interval. The breathing sensing device 10''' may set the average values of a plurality of breathing intervals as a representative breathing interval of the user.

The breathing sensing device 10''' may verify the apnea time period by determining whether the third signal measured in the t10 in FIG. 12A has a gentle slope without increasing the measured values. The respiratory sensing device 10''' may determine whether the respiration time of the third signal has not been detected in the apnea period calculated through the first and second signals. The respiratory sensing device 10''' may determine whether the apnea period calculated through the first and second signals and the apnea period calculated from the third signal coincide temporally.

The respiratory sensing device 10''' may set, with respect to the third signal, a time period with a slope value greater than the 3-1 reference value as inspiration time period, and a time period with a slope value less than the 3-2 reference value as exhalation time period. A time period having a slope value between the 3-1 reference value and the 3-2 reference value may be determined as the apnea period. The 3-1 and 3-2 reference values may be determined by the third signal measured for the user.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A respiratory sensing device comprising:

a housing including a structure in an inner space thereof, wherein a processing main board is provided in the structure;

a flexible substrate, wherein the housing is disposed on and connected to one surface of the flexible substrate and a plurality of respiration sensor electrodes are disposed on the flexible substrate; and an adhesive member having a certain-predetermined thickness, including an opening portion through which the plurality of respiration sensor electrodes are exposed, disposed on another surface of the flexible substrate, and configured to attach the flexible substrate to skin, wherein the plurality of respiration sensor electrodes are spaced apart from the skin by the predetermined thickness of the adhesive member, such that air is interposed between the plurality of respiration sensor electrodes and the skin through the opening portion, wherein the plurality of respiration sensor electrodes are configured to measure a first capacitance value that changes as the air decreases when an abdomen expands during an inspiration phase of respiration, and measure a second capacitance value that changes as the air layer increases when the abdomen contracts during an expiration phase of the respiration, wherein the processing main board is configured to:

determine an expiration time point and an inspiration time point of the respiration based on a signal measured by at least one of the plurality of respiration sensor electrodes, and analyze the signal to identify at least one characteristic of the signal that varies over time, and to determine a plurality of respiration-related time intervals based on the at least one characteristic.

2. The respiratory sensing device of claim 1, wherein the plurality of respiration sensor electrodes are located on the flexible substrate in an area where the housing is not located.

3. The respiratory sensing device of claim 1, further comprising a cover member arranged to cover the one opening portion and implemented with a high dielectric elastic material.

4. The respiratory sensing device of claim 1, wherein the flexible substrate further comprises at least one electrocardiogram electrode at a position corresponding to the housing.

5. The respiratory sensing device of claim 4, wherein the adhesive member further comprises a conductive hole area at a position corresponding to the at least one electrocardiogram electrode to allow the at least one electrocardiogram electrode to be electrically connected to the skin.

6. The respiratory sensing device of claim 5, wherein the conductive hole area is filled with a hydrogel material.

7. The respiratory sensing device of claim 1, wherein the plurality of respiration sensor electrodes are not directly attached to the skin through the one opening portion.

8. The respiratory sensing device of claim 1, further comprising a connection portion disposed on the flexible substrate.

9. The respiratory sensing device of claim 8, wherein the respiratory sensing device is further electrically connected to at least one of an external temperature sensor, an acceleration sensor, a microphone, and an electrocardiogram sensor through the connection portion to receive measurement values.

10. The respiratory sensing device of claim 8, wherein the respiratory sensing device is further connected to an external nasal breathing device through the connection portion to check signals of exhalation air and inhalation air of user's nose.

11. The respiratory sensing device of claim 1, wherein the housing is arranged on the flexible substrate in a direction perpendicular to a direction in which the plurality of respiration sensor electrodes are arranged in a row.

12. The respiratory sensing device of claim 1, wherein the plurality of respiration sensor electrodes and the housing are arranged on the flexible substrate in a row.

13. A method of using the respiratory sensing device of claim 1, comprising attaching, through the adhesive member, the plurality of respiration sensor electrodes of the flexible substrate at a height of a portion around a user's abdomen.

14. A method of using the respiratory sensing device of claim 1, comprising attaching, through the adhesive member, the plurality of respiration sensor electrodes of the flexible substrate at a height of a portion around a user's chest.

15. The respiratory sensing device of claim 1, wherein the predetermined thickness of the adhesive member is at least 0.5 mm.

16. The respiratory sensing device of claim 1, wherein the flexible substrate includes a first region and a second region extending from the first region in a longitudinal direction, and wherein the housing is disposed on the first region and wherein the plurality of respiration sensor electrodes are disposed on the second region.

17. The respiratory sensing device of claim 1, wherein the flexible substrate includes a bend at a predetermined angle in a range of 45 degrees to 135 degrees, defining a first region and a second region extending from the first region at the predetermined angle, and wherein the housing is disposed on the first region and the plurality of respiration sensor electrodes are disposed on the second region.

18. The respiratory sensing device of claim 17, wherein the predetermined angle is 90 degrees, thereby defining an L-shaped architecture.

* * * * *